(12) United States Patent
Takiguchi

(10) Patent No.: US 10,466,458 B2
(45) Date of Patent: Nov. 5, 2019

(54) IMAGE ACQUISITION DEVICE, IMAGE ACQUISITION METHOD, AND SPATIAL LIGHT MODULATION UNIT

(71) Applicant: HAMAMATSU PHOTONICS K.K., Hamamatsu-shi, Shizuoka (JP)

(72) Inventor: Yuu Takiguchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/772,648

(22) PCT Filed: Sep. 20, 2016

(86) PCT No.: PCT/JP2016/077689
§ 371 (c)(1),
(2) Date: May 1, 2018

(87) PCT Pub. No.: WO2017/077777
PCT Pub. Date: May 11, 2017

(65) Prior Publication Data
US 2019/0137744 A1 May 9, 2019

(30) Foreign Application Priority Data
Nov. 6, 2015 (JP) .................. 2015-218527

(51) Int. Cl.
*G01N 21/64* (2006.01)
*G02B 21/00* (2006.01)
(Continued)

(52) U.S. Cl.
CPC ......... *G02B 21/0052* (2013.01); *G01N 21/64* (2013.01); *G01N 21/6428* (2013.01);
(Continued)

(58) Field of Classification Search
CPC ............ G02B 21/0052; G02B 21/6428; G02B 21/6458; G02B 21/0032; G02B 21/16;
(Continued)

(56) References Cited

U.S. PATENT DOCUMENTS 6,525,875 B1 * 2/2003 Lauer ............... G03H 1/0443
359/368
6,775,009 B2 * 8/2004 Hill .................. B82Y 20/00
356/511
(Continued)

FOREIGN PATENT DOCUMENTS

JP    2014-59511 A    4/2014
JP    2015-135463 A   7/2015
(Continued)

OTHER PUBLICATIONS

Florian O. Fahrbach et al., "A line scanned light-sheet microscope with phase shaped self-reconstructing beams," Optics Express, Nov. 8, 2010, pp. 24229-24244, vol. 18, No. 23.
(Continued)

*Primary Examiner* — Marcus H Taningco
*Assistant Examiner* — Djura Malevic
(74) *Attorney, Agent, or Firm* — Drinker Biddle & Reath LLP

(57) ABSTRACT

An image acquisition device includes a light source, a spatial light modulator having a plurality of pixels two-dimensionally arranged and fro modulating a phase of excitation light output from the light source for each of the plurality of pixels, a first objective lens, a second objective lens, a photodetector, and a control unit for controlling an amount of phase modulation for each of the plurality of pixels in accordance with a two-dimensional phase pattern corresponding to the plurality of pixels. The phase pattern is generated based on a predetermined basic phase pattern. The basic phase pattern includes a first region in which the phase value continuously increases in a predetermined direction and a second region in which the phase value continuously decreases in the direction and facing the first region in the direction.

12 Claims, 11 Drawing Sheets

(51) Int. Cl.
*G02B 21/16* (2006.01)
*G02B 21/36* (2006.01)

(52) U.S. Cl.
CPC ..... *G01N 21/6458* (2013.01); *G02B 21/0032* (2013.01); *G02B 21/16* (2013.01); *G02B 21/361* (2013.01); *G02B 21/367* (2013.01); *G01N 2021/6439* (2013.01); *G01N 2021/6463* (2013.01); *G01N 2201/063* (2013.01)

(58) Field of Classification Search
CPC ......... G02B 21/361; G01N 2021/6439; G01N 2021/6463; G01N 2021/063; G01N 21/64; G01N 21/6428; G01N 21/6458; G02F 1/37; G02F 1/1337
See application file for complete search history.

(56) References Cited

U.S. PATENT DOCUMENTS

| | | | |
|---|---|---|---|
| 8,836,948 B2* | 9/2014 | Liu | G01B 9/04 356/445 |
| 2002/0122246 A1* | 9/2002 | Tearney | A61B 1/00096 359/368 |
| 2006/0033987 A1* | 2/2006 | Stelzer | G02B 21/06 359/385 |
| 2007/0109633 A1* | 5/2007 | Stelzer | G02B 21/06 359/385 |
| 2009/0116707 A1* | 5/2009 | Sutko | G06K 9/00134 382/128 |
| 2009/0225413 A1* | 9/2009 | Stelzer | G02B 21/06 359/385 |
| 2012/0049087 A1* | 3/2012 | Choi | G01N 21/4795 250/459.1 |
| 2012/0056996 A1* | 3/2012 | Sander | G02B 21/16 348/47 |
| 2012/0133937 A1* | 5/2012 | Heintzmann | G01J 3/02 356/364 |
| 2014/0008525 A1* | 1/2014 | Simon | G02B 21/0056 250/226 |
| 2014/0042339 A1* | 2/2014 | Stelzer | G02B 21/06 250/459.1 |
| 2015/0168732 A1* | 6/2015 | Singer | G02B 21/0032 348/79 |
| 2015/0177506 A1* | 6/2015 | Nishiwaki | G02B 21/367 348/46 |
| 2015/0219980 A1* | 8/2015 | Saito | G02B 5/3091 349/123 |
| 2015/0260978 A1* | 9/2015 | Cremer | G02B 21/0004 348/79 |
| 2016/0202178 A1* | 7/2016 | Acosta | G01N 21/27 356/303 |
| 2016/0305883 A1* | 10/2016 | Betzig | G02B 21/16 |
| 2016/0327779 A1* | 11/2016 | Hillman | G02B 21/367 |
| 2017/0176338 A1* | 6/2017 | Wu | G06T 7/90 |

FOREIGN PATENT DOCUMENTS

| | | |
|---|---|---|
| JP | 2015-159541 A | 9/2015 |
| JP | 2015-527604 A | 9/2015 |
| WO | WO-2014/005682 A2 | 1/2014 |

OTHER PUBLICATIONS

International Preliminary Report on Patentability dated May 17, 2018 for PCT/JP2016/077689.

Li Runze et al, "Selective plane illumination microscopy with structured illumination based on spatial light modulators", Progress in Biomedical Optics and Imaging, SPIE—International Society for Optical Engineering, Bellingham, WA, US, vol. 8949, Mar. 12, 2014, p89491S, XP060033925.

B.-C. Chen. et al, "Lattice light-sheet microscopy: Imaging molecules to embryos at high spatiotemporal resolution", Science, vol. 346, No. 6208, Oct. 23, 2014, p1257998, XP055277112.

* cited by examiner

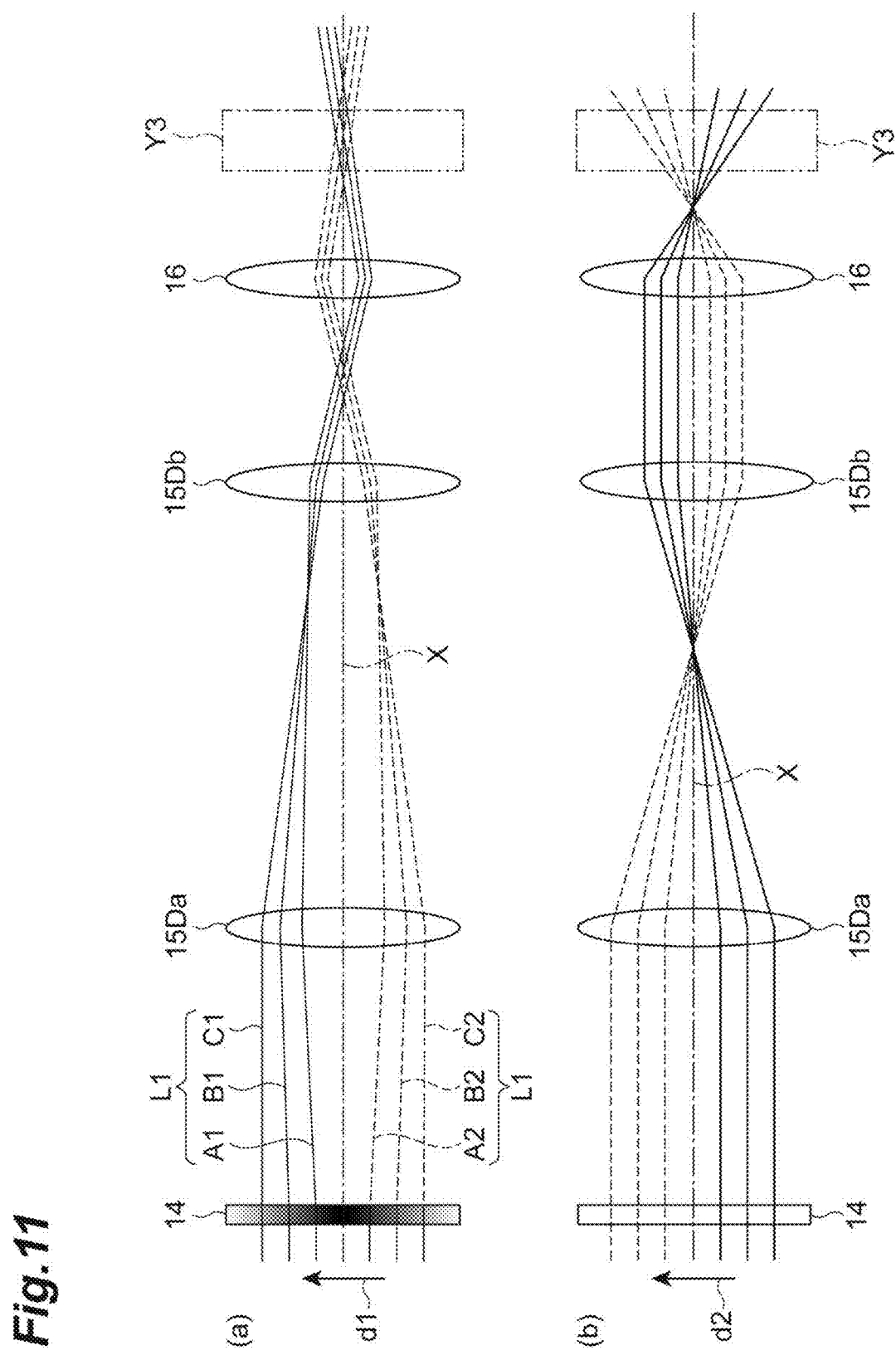

IMAGE ACQUISITION DEVICE, IMAGE ACQUISITION METHOD, AND SPATIAL LIGHT MODULATION UNIT

TECHNICAL FIELD

An aspect of the present invention relate to an image acquisition device, an image acquisition method, and a spatial light modulation unit for acquiring an image by capturing detection light emitted from a sample in association with irradiation of excitation light.

BACKGROUND ART

As such an image acquisition device, there is a light-sheet microscope that irradiates sheet-like excitation light to a sample and captures detection light emitted from the sample in association with irradiation of the excitation light (see, for example, the following Non-Patent Literature 1). In the light-sheet microscope described in Non-Patent Literature 1, it is possible to produce pseudo sheet-like excitation light by generating a Bessel beam by a spatial light modulator (SLM) and scanning a light focus point of the generated Bessel beam along its optical axis.

CITATION LIST

Non-Patent Literature

[Non-Patent Literature 1] Florian O. Fahrbach and Alexander Rohrbach, "A line Scanned light-sheet microscope with phased shaped self-reconstructing beams", November 2010/Vol. 18, No. 23/OPTICS EXPRESS pp. 24229-24244

SUMMARY OF INVENTION

Technical Problem

In the light-sheet microscope described in the above-described Non-Patent Literature 1, optical elements for scanning or the like are required because sheet-like excitation light is generated in a pseudo manner by scanning the light focus point of the Bessel beam along the optical axis. Thus, there is a possibility of a device configuration becoming complicated.

An objective of an aspect of the present invention is to provide an image acquisition device, an image acquisition method, and a spatial light modulation unit capable of generating sheet-like excitation light with a simple configuration.

Solution to Problem

According to an aspect of the present invention, an image acquisition device includes a light source for outputting excitation light including a wavelength for exciting a sample; a spatial light modulator having a plurality of pixels two-dimensionally arranged and for modulating a phase of the excitation light output from the light source for each of the plurality of pixels; a first objective lens for radiating the excitation light modulated by the spatial light modulator to the sample; a second objective lens for guiding detection light emitted from the sample in association with irradiation of the excitation light from the first objective lens; a photodetector for capturing an image of the detection light guided by the second objective lens; and a control unit for controlling an amount of phase modulation for each of the plurality of pixels in accordance with a phase pattern in which phase values corresponding to the plurality of pixels are two-dimensionally distributed, wherein the phase pattern is a phase pattern generated based on a predetermined basic phase pattern, and wherein the basic phase pattern includes a first region in which the phase value continuously increases in a predetermined direction and a second region in which the phase value continuously decreases in the predetermined direction and facing the first region in the predetermined direction.

In the image acquisition device, the phase pattern is calculated based on the basic phase pattern including the first region in which the phase value continuously increases in the predetermined direction and the second region in which the phase value continuously decreases in the predetermined direction. It is possible to radiate sheet-like excitation light from the first objective lens to the sample by modulating the excitation light in the spatial light modulator in accordance with the phase pattern. Accordingly, it is unnecessary to scan a light focus point of a Bessel beam in order to generate sheet-like excitation light as in the conventional technology, and an optical element or the like for the scanning can be omitted. Consequently, according to the image acquisition device, it is possible to generate sheet-like excitation light with a simple configuration.

In the image acquisition device according to an aspect of the present invention, the phase value may linearly increase in the predetermined direction in the first region and the phase value may linearly decrease in the predetermined direction in the second region. Accordingly, because the basic phase pattern is simplified, it is possible to generate sheet-like excitation light with a simpler configuration without using a complex optical element or the like.

In the image acquisition device according to an aspect of the present invention, the basic phase pattern may be axisymmetric with respect to a straight line passing through a center in the predetermined direction and orthogonal to the predetermined direction. Accordingly, it is possible to generate sheet-like excitation light on an optical axis of the first objective lens. Therefore, optical axis adjustment of the first objective lens and the second objective lens is facilitated.

In the image acquisition device according to an aspect of the present invention, the basic phase pattern may be non-axisymmetric with respect to a straight line passing through a center in the predetermined direction and orthogonal to the predetermined direction. Accordingly, it is possible to generate sheet-like excitation light at a position different from that on an optical axis of the first objective lens.

In the image acquisition device according to an aspect of the present invention, the first region and the second region may be adjacent to each other and the phase values may be continuous at a boundary therebetween. Accordingly, because the basic phase pattern is simplified, it is possible to generate sheet-like excitation light with a simpler configuration without using a complex optical element or the like.

In the image acquisition device according to an aspect of the present invention, the phase pattern may be a phase pattern in which a diffraction grating pattern of a diffraction grating shape and the basic phase pattern are superimposed on each other. Accordingly, it is possible to form the phase of the excitation light in the diffraction grating shape without providing a diffraction grating. Thus, it is possible to generate sheet-like excitation light with a simpler configuration.

In the image acquisition device according to an aspect of the present invention, the phase pattern may be a phase pattern in which a lens pattern of a lens shape and the basic phase pattern are superimposed on each other. Accordingly, it is possible to form a phase of the excitation light in a lens shape without providing a lens element. Thus, it is possible to generate sheet-like excitation light with a simpler configuration.

According to an aspect of the present invention, the image acquisition device may further include a light scanning unit for scanning the sample with the excitation light.

In the image acquisition device according to an aspect of the present invention, the photodetector may be a two-dimensional imaging element having a plurality of pixel columns and in which rolling reading is enabled. Accordingly, it is possible to improve S/N ratio as compared with when a two-dimensional imaging element in which global reading is enabled is used.

According to an aspect of the present invention, an image acquisition method includes a first step of modulating, by a spatial light modulator having a plurality of pixels two-dimensionally arranged, a phase of the excitation light including a wavelength for exciting a sample for each of the plurality of pixels; a second step of radiating the excitation light modulated by the spatial light modulator to the sample; and a third step of guiding detection light emitted from the sample in association with irradiation of the excitation light and capturing an image of the guided detection light, wherein the first step includes controlling an amount of phase modulation for each of the plurality of pixels in accordance with a phase pattern generated based on a predetermined basic phase pattern and in which phase values corresponding to the plurality of pixels are two-dimensionally distributed, and wherein the basic phase pattern includes a first region in which the phase value continuously increases in a predetermined direction and a second region in which the phase value continuously decreases in the predetermined direction and facing the first region in the predetermined direction.

In the image acquisition method, the phase pattern is calculated based on the basic phase pattern including the first region in which the phase value continuously increases in the predetermined direction and a second region in which the phase value continuously decreases in the predetermined direction. It is possible to radiate sheet-like excitation light to the sample by modulating the excitation light in the spatial light modulator in accordance with the phase pattern. Accordingly, it is unnecessary to scan a light focus point of a Bessel beam in order to generate sheet-like excitation light as in the conventional technology, and an optical element or the like for the scanning can be omitted. Consequently, according to the image acquisition method, it is possible to generate sheet-like excitation light with a simple configuration.

According to an aspect of the present invention, a spatial light modulation unit for use in a light-sheet microscope includes a spatial light modulator having a plurality of pixels two-dimensionally arranged and for modulate a phase of input light for each of the plurality of pixels and output the modulated light; and a control unit for control an amount of phase modulation for each of the plurality of pixels in accordance with a phase pattern in which phase values corresponding to the plurality of pixels are two-dimensionally distributed, wherein the phase pattern is a phase pattern generated based on a predetermined basic phase pattern, and wherein the basic phase pattern has a first region in which the phase value continuously increases in a predetermined direction and a second region facing the first region in the predetermined direction and in which the phase value continuously decreases in the predetermined direction.

In the spatial light modulation unit, the phase pattern is calculated based on the basic phase pattern having the first region in which the phase value continuously increases in the predetermined direction and a second region in which the phase value continuously decreases in the predetermined direction. It is possible to radiate sheet-like excitation light to the sample by modulating the excitation light in the spatial light modulator in accordance with the phase pattern. Accordingly, it is unnecessary to scan a light focus point of a Bessel beam in order to generate sheet-like excitation light as in the conventional technology, and an optical element or the like for the scanning can be omitted. Consequently, according to the spatial light modulation unit, it is possible to generate sheet-like excitation light with a simple configuration.

Advantageous Effects of Invention

According to one aspect of the present invention, sheet-like excitation light can be generated with a simple configuration.

BRIEF DESCRIPTION OF DRAWINGS

FIG. 11 is a conceptual diagram illustrating a state in which sheet-like excitation light is generated in the light-sheet microscope of FIG. 10.

DESCRIPTION OF EMBODIMENTS

Hereinafter, embodiments of an image acquisition device and an image acquisition method of the present invention will be described in detail with reference to the drawings. In the following description, the same reference signs are used for the same or corresponding elements, and redundant description thereof will be omitted.

Figure 1:
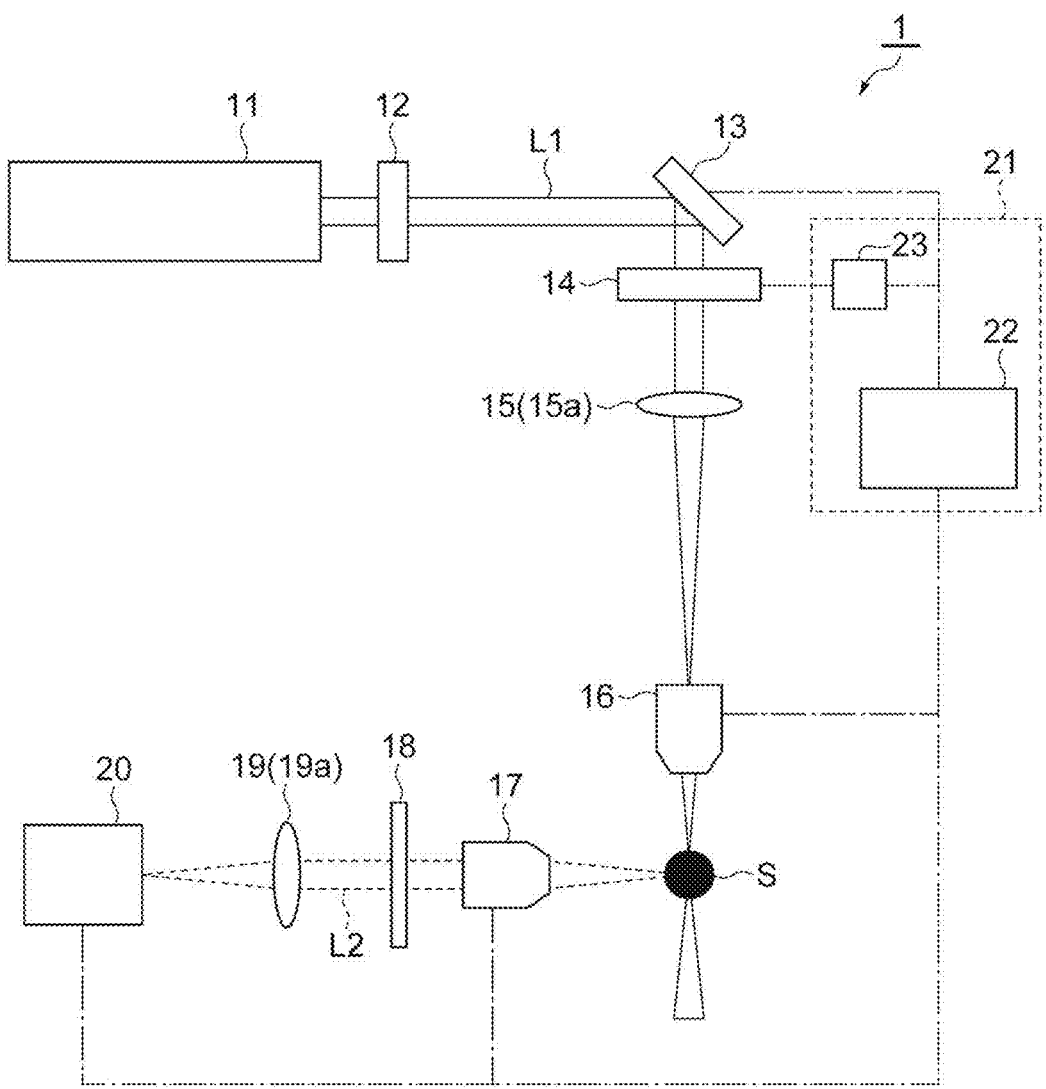
FIG. 1 is a block diagram illustrating a configuration of a light-sheet microscope which is an embodiment of an image acquisition device of the present invention.

A light-sheet microscope (an image acquisition device) 1 illustrated in FIG. 1 is a device configured to acquire an image of a sample S by irradiating the sample S with sheet-like excitation light L1 and forming an image of detection light L2 emitted from the sample S in accordance with the irradiation of the excitation light L1. In the light-sheet microscope 1, a light focus position of the excitation light L1 is scanned with respect to the sample S in a direction orthogonal to an optical axis of the excitation light L1, and the image of the sample S is acquired at each light focus position. In the light-sheet microscope 1, because a region in which the excitation light L1 is radiated to the sample S is small, deterioration of the sample S such as photofading or phototoxicity can be minimized and image acquisition can be speeded up.

The sample S to be observed is, for example, a sample such as a biological cell or organism containing a fluorescent substance such as a fluorescent dye or a fluorescent gene. For example, the sample S emits the detection light L2 such as fluorescence when light of a predetermined wavelength range is radiated. For example, the sample S is accommodated in a holder having at least transparency to the excitation light L1 and the detection light L2. This holder is held on, for example, a stage.

As illustrated in FIG. 1, the light-sheet microscope 1 includes a light source 11, a collimator lens 12, a light scanning unit 13, a spatial light modulator (SLM) 14, a first optical system 15, a first objective lens 16, a second objective lens 17, a filter 18, a second optical system 19, a photodetector 20, and a control unit 21.

The light source 11 outputs excitation light L1 including a wavelength for exciting the sample S. For example, the light source 11 emits coherent light or incoherent light. Examples of the coherent light source include a laser light source such as a laser diode (LD). Examples of the incoherent light source include a light emitting diode (LED), a super luminescent diode (SLD), a lamp type light source, and the like. As the laser light source, a light source configured to oscillate continuous waves is preferable and a light source configured to oscillate pulsed light such as ultrashort pulsed light may be used. As a light source configured to oscillate pulsed light, a unit in which a light source configured to output pulsed light and an optical shutter or an acousto-optic modulator (AOM) for pulse modulation are combined may be used. The light source 11 may be configured to output the excitation light L1 including a plurality of wavelength ranges. In this case, some of wavelengths of the excitation light L1 may be selectively transmitted by an optical filter such as an acousto-optic tunable filter.

The collimator lens 12 collimates the excitation light L1 output from the light source 11 and outputs the collimated excitation light L1. The optical scanning unit 13 is an optical scanner configured to scan the sample S with the excitation light L1 by changing a traveling direction of the excitation light L1 output from the collimator lens 12. Thereby, scanning is performed on a surface of the sample S in a direction in which irradiation positions of the excitation light L1 with which the sample S is irradiated via the first optical system 15 and the first objective lens 16 are orthogonal to the optical axis of the first objective lens 16 (the optical axis of the excitation light L1). The optical scanning unit 13 is, for example, a galvanometer mirror, a resonant scanner, a polygon mirror, a micro electro mechanical system (MEMS) mirror, an acousto-optic device such as an AOM or an acousto-optic deflector (AOD), or the like.

The SLM 14 is a phase modulation type spatial light modulator having a plurality of pixels two-dimensionally arranged and configured to modulate the phase of the excitation light L1 output from the light source 11 for each of the plurality of pixels. The SLM 14 modulates the excitation light L1 incident from the optical scanning unit 13 and outputs the modulated excitation light L1 to the first optical system 15 (a first step or a modulation step). The SLM 14 is configured as, for example, a transmission type or a reflection type. In FIG. 1, a transmission type SLM 14 is illustrated. The SLM 14 is, for example, a refractive index changing material type SLM (for example, a liquid crystal on silicon (LCOS) type SLM or a liquid crystal display (LCD)), a variable mirror type SLM (for example, a segment mirror type SLM or a continuous deformable mirror type SLM), an SLM using an electrical address type liquid crystal element or an optical address type liquid crystal element, or the like. The SLM 14 is electrically connected to the controller 23 of the control unit 21 and constitutes a spatial light modulation unit. The driving of the SLM 14 is controlled by the controller 23. Details of the control of the SLM 14 by the control unit 21 will be described below.

The first optical system 15 optically couples the SLM 14 and the first objective lens 16 so that the excitation light L1 output from the SLM 14 is guided to the first objective lens 16. Here, the first optical system 15 includes a lens 15a for focusing the excitation light L1 from the SLM 14 on the pupil of the first objective lens 16 and constitutes a both-side telecentric optical system.

The first objective lens 16 is an objective lens for illumination, and irradiates the sample S with the excitation light L1 modulated by the SLM 14 (a second step or an irradiation step). The first objective lens 16 is movable along its optical axis by a driving element such as a piezoelectric actuator or a stepping motor. Thereby, the light focus position of the excitation light L1 can be adjusted. Also, the first optical system 15 and the first objective lens 16 constitute an irradiation optical system.

The second objective lens 17 is an objective lens for detection and guides the detection light L2 emitted from the sample S in accordance with the irradiation of the excitation light L1 from the first objective lens 16 to the photodetector 20 side. In this example, the second objective lens 17 is arranged so that its optical axis (the optical axis of the detection light L2) and the optical axis of the first objective lens 16 are orthogonal to (intersect) each other. The second objective lens 17 can be moved along its optical axis by a drive element such as a piezoelectric actuator or a stepping motor. Thereby, a focal position of the second objective lens 17 can be adjusted.

Figure 2:
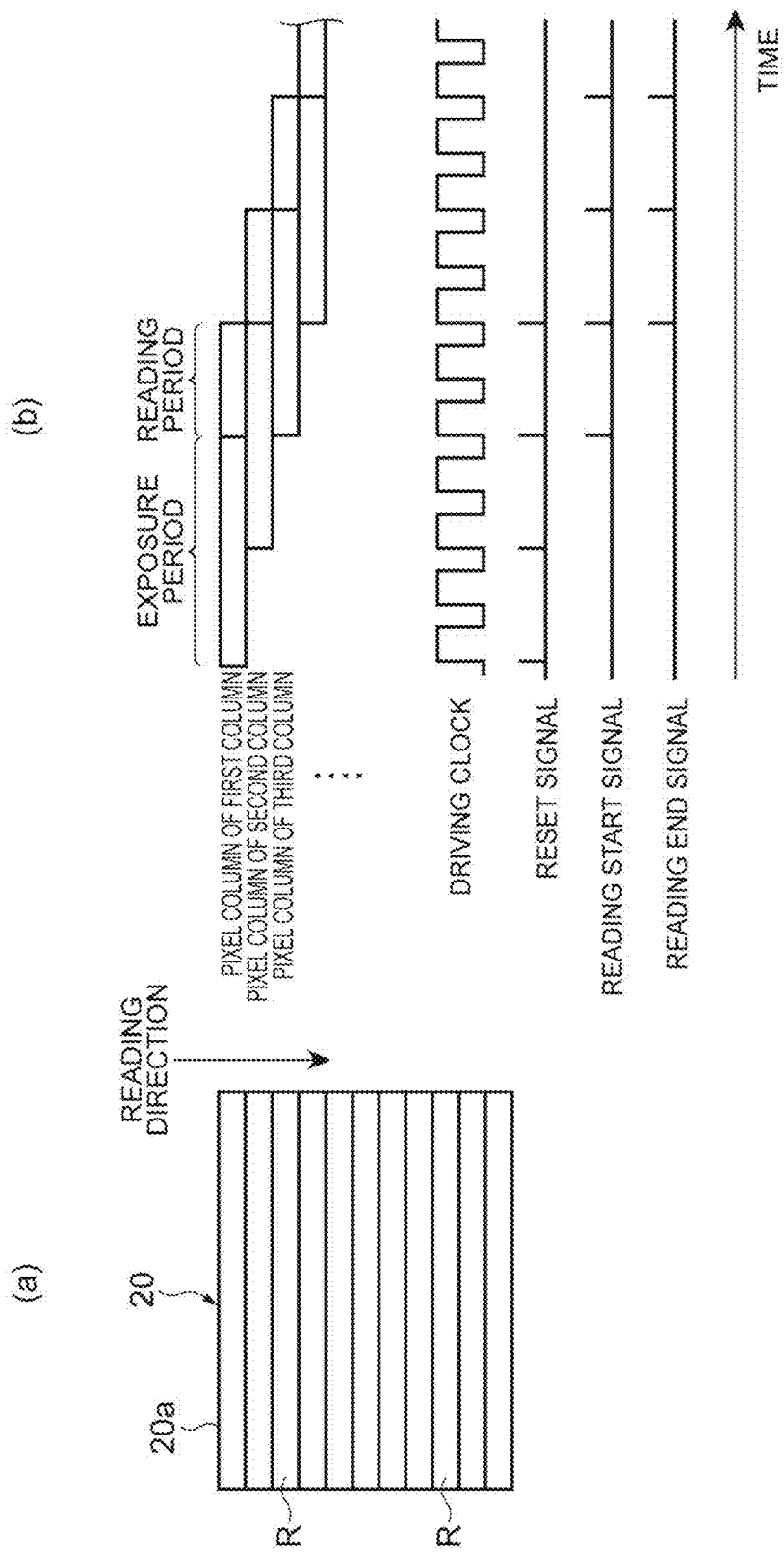
FIG. 2(a) is a diagram illustrating a light receiving surface of the photodetector of FIG. 1.
FIG. 2(b) is a diagram illustrating rolling reading in a photodetector.

The filter 18 is an optical filter for separating the excitation light L1 and the detection light L2 from the light guided by the second objective lens 17 and outputting the extracted detection light L2 to the photodetector 20 side. The filter 18 is arranged on an optical path between the second objective lens 17 and the photodetector 20. The second optical system 19 optically couples the second objective lens 17 and the photodetector 20 so that the detection light L2 output from the second objective lens 17 is guided to the photodetector 20. The second optical system 19 includes a lens 19a for forming the image of the detection light L2 from the second objective lens 17 on a light receiving surface 20a (FIG. 2) of the photodetector 20. Also, the second optical system 19 and the second objective lens 17 constitute a detection optical system.

The photodetector 20 captures an image of the detection light L2 guided by the second objective lens 17 and formed on the light receiving surface 20a (a third step or an imaging step). The photodetector 20 is a two-dimensional imaging element having a plurality of pixel columns and in which rolling reading is possible for each of the plurality of pixel columns. An example of such a photodetector 20 is a CMOS image sensor or the like. As illustrated in FIG. 2(a), on the light receiving surface 20a of the photodetector 20, a plurality of pixel columns R in which a plurality of pixels are arranged in a direction perpendicular to a reading direction are arranged in the reading direction.

In the photodetector 20, as illustrated in FIG. 2(b), exposure and reading are controlled for each pixel column R by inputting a reset signal and a reading start signal based on a driving cycle of a driving clock. In the rolling reading, the reading start signal is sequentially input for each pixel column R with a predetermined time difference. Thus, unlike global reading in which all pixel columns are simultaneously read, reading for each pixel column R is sequentially performed with a predetermined time difference.

The control unit 21 includes a computer 22 including a processor, a memory and the like, and a controller 23 including a processor, a memory, and the like. The computer 22 is, for example, a personal computer or a smart device, and by the processor, controls operations of the optical scanning unit 13, the first objective lens 16, the second objective lens 17, the photodetector 20, the controller 23, and the like and executes various types of control. For example, the computer 22 may perform control for synchronizing a timing of scanning of the excitation light L1 by the optical scanning unit 13 with a timing of imaging of the detection light L2 by the photodetector 20. Specifically, the detection light L2 detected by the photodetector 20 also moves in accordance with the scanning of the excitation light L1 by the optical scanning unit 13. Thus, the computer 22 controls the photodetector 20 or the optical scanning unit 13 so that signal reading by rolling reading is performed in accordance with the movement of the detection light L2 in the photodetector 20.

Figure 3:
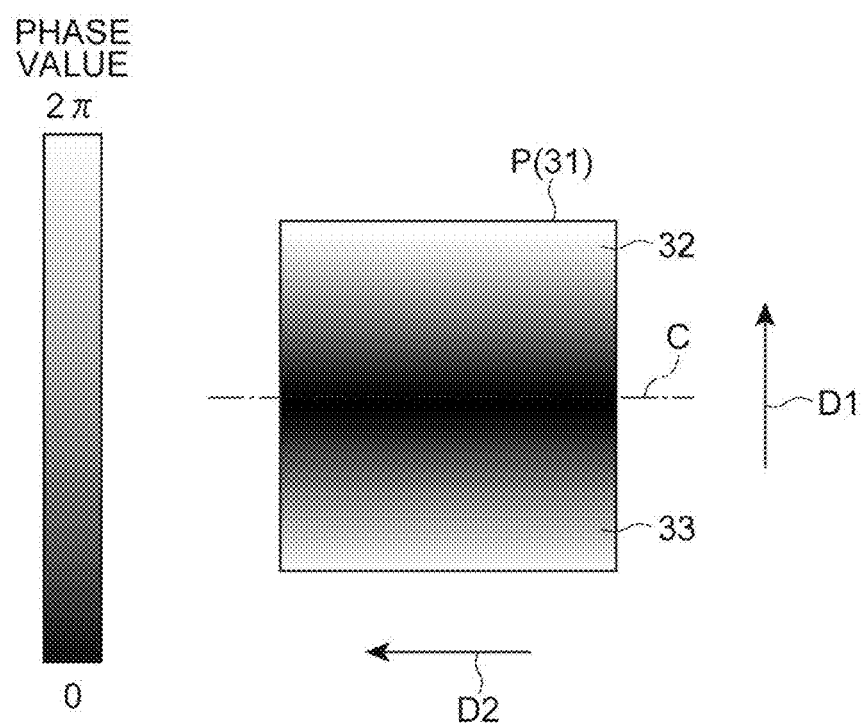
FIG. 3 is a diagram illustrating a basic phase pattern used in the light-sheet microscope of FIG. 1.

The controller 23 is electrically connected to the computer 22, and controls an amount of phase modulation for each of the plurality of pixels in the SLM 14 in accordance with a two-dimensional phase pattern P as illustrated in FIG. 3. The phase pattern P is a pattern of phase values related to positions on a two-dimensional plane and the positions in the phase pattern P correspond to a plurality of pixels of the SLM 14. A phase value of the phase pattern P is defined between 0 and $2\pi$ radians. In FIG. 3, the phase value in each part of the phase pattern P is represented by a color depth. Also, an upper limit of the phase value of the phase pattern P may be larger than $2\pi$ radians.

For each pixel of the SLM 14, the controller 23 controls the amount of phase modulation of the pixel in accordance with the phase value at the position corresponding to the pixel in the phase pattern P. Specifically, for example, within the controller 23, a D/A conversion unit (a digital/analog converter) such as a digital video interface (DVI) configured to convert a phase value of a phase pattern P input as digital data into a driving voltage value to be applied to each pixel is provided. When the phase pattern P is input from the computer 22 to the controller 23, the controller 23 converts the phase value of the phase pattern P into the driving voltage value by using the D/A conversion unit and inputs the driving voltage value to the SLM 14. The SLM 14 applies a voltage to each pixel in accordance with the input driving voltage value. For example, the SLM 14 may include a D/A conversion unit, and the controller 23 may input digital data according to the phase pattern P to the SLM 14. In this case, the phase value of the phase pattern P is converted into the driving voltage value by the D/A conversion unit of the SLM 14. Also, instead of performing the D/A conversion, the SLM 14 may control a voltage value to be applied to each pixel based on the digital signal output from the controller 23.

The phase pattern P is calculated by the computer 22 of the control unit 21 based on the predetermined basic phase pattern 31. For example, the basic phase pattern 31 may be pre-stored in the memory of the computer 22. By modulating the excitation light L1 with the SLM 14 in accordance with the phase pattern P calculated based on the basic phase pattern 31, it is possible to radiate the sheet-like excitation light L1 from the first objective lens 16. Although the phase pattern P may be calculated by further superimposing another pattern on the basic phase pattern 31 as will be described below, a case in which the basic phase pattern 31 used as the phase pattern P as it is will be described hereinafter.

As illustrated in FIG. 3, the basic phase pattern 31 is set within a rectangular range. The basic phase pattern 31 has a rectangular first region 32 in which the phase value continuously increases in a predetermined direction D1 and a rectangular second region 33 facing the first region 32 in the direction D1 and in which the phase value continuously decreases in the direction D1. That is, in the first region 32 and the second region 33, the directions in which the phase value increases and decreases are opposite to each other. The fact that the "phase value continuously increases" in a certain region indicates that the phase values are continuous without interruption across the entire region. Also, a case in which the phase value is 0 radians and a case in which the phase value is $2\pi$ radians indicate the same state, and the phase value is continuous even if the phase value varies between 0 radians and $2\pi$ radians.

In the first region 32, the phase value linearly increases in the direction D1. In the second region 33, the phase value linearly decreases in the direction D1. In both of the first region 32 and the second region 33, the phase value changes by $2\pi$ radians. That is, an absolute value of a gradient (a rate of increase) of the phase value in the first region 32 is equal to an absolute value of a gradient (a rate of decrease) of the phase value in the second region 33. In both of the first region 32 and the second region 33, the phase value is constant in a direction D2 orthogonal to the direction D1. The first region 32 and the second region 33 are adjacent to each other and the phase value is continuous at a boundary therebetween. In this example, the phase value at the boundary is 0 radians. The basic phase pattern 31 is axisymmetric with respect to a straight line (a central line) C passing through the center in the direction D1 and orthogonal to the direction D1. In this example, the boundary between the first region 32 and the second region 33 is located on the central line C.

Figure 4:
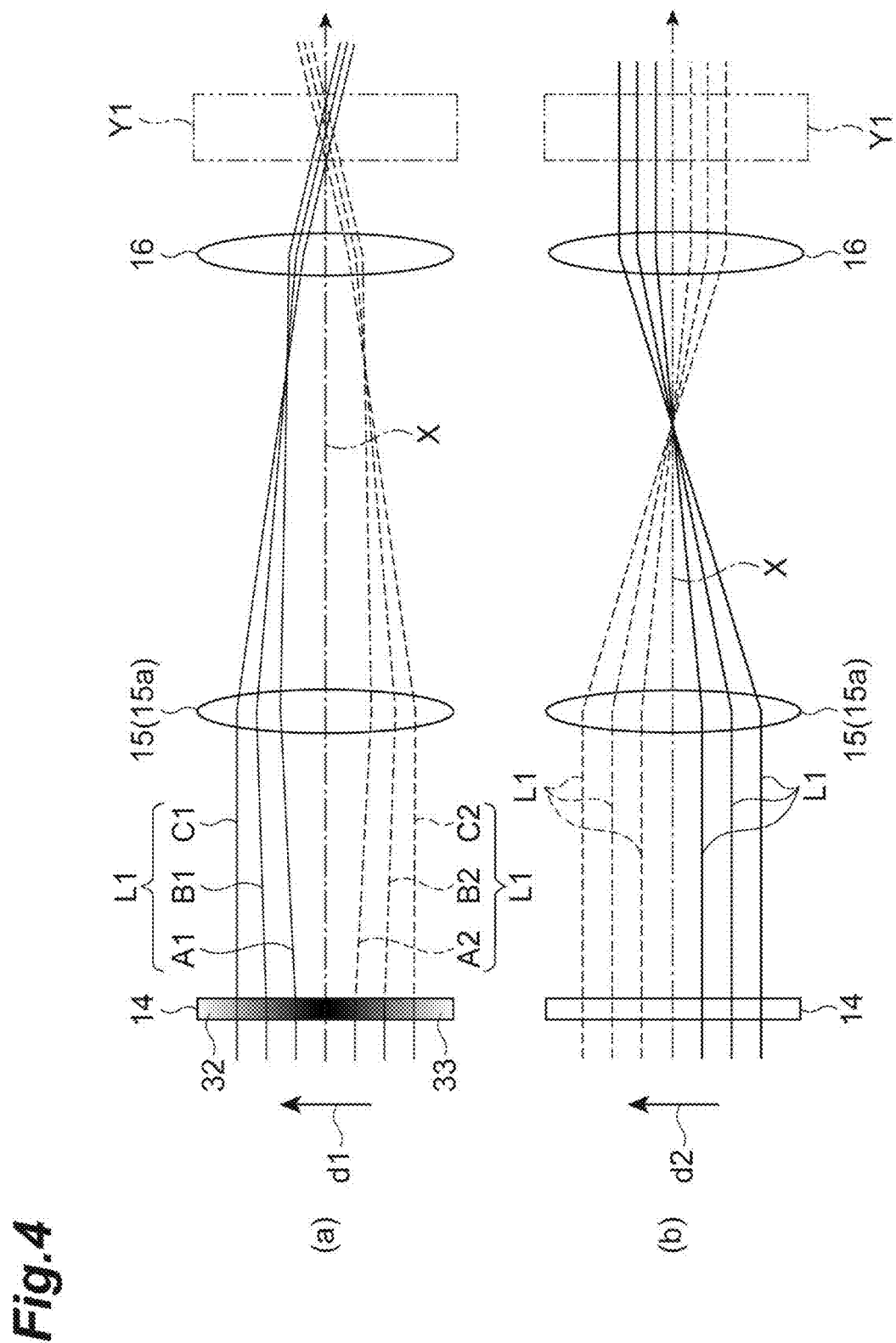
FIG. 4 is a conceptual diagram illustrating a state in which sheet-like excitation light is generated.

FIG. 4 is a conceptual diagram illustrating a state in which sheet-like excitation light L1 is generated by the excitation light L1 modulated by the SLM 14 in accordance with the basic phase pattern 31. FIG. 4(a) is a diagram illustrating an optical path of the excitation light L1 when viewed from a direction d2 corresponding to a direction D2 and FIG. 4(b) is a diagram illustrating an optical path of the excitation light L1 when viewed from a direction d1 corresponding to a direction D1. In FIG. 4(a), three pieces of excitation light A1, B1, and C1 in ascending order of distances from an optical axis X of the first objective lens 16 are illustrated as an example of the optical path of the excitation light L1 incident on the first region 32. Also, three pieces of excitation light A2, B2, and C2 in ascending order of distances from the optical axis X are illustrated as an example of the optical path of the excitation light L1 incident on the second region 33.

As illustrated in FIG. 4(a), phases of the excitation light A1 and A2 are delayed by a predetermined amount in the SLM 14 and images thereof are formed on the optical axis X. Amounts of phase delay in the excitation light B1 and B2 in the SLM 14 are larger than those in the excitation light A1 and A2. Thus, images of the excitation light B1 and B2 are formed on the optical axis X at positions farther from the first objective lens 16 than those of the excitation light A1 and A2. Amounts of phase delay in the excitation light C1 and C2 in the SLM 14 are smaller than that in the excitation light A1 and A2, and the phase does not substantially change in the SLM 14. Thus, images of the excitation light C1 and C2 are formed on the optical axis X at position closer to the first objective lens 16 than those of the excitation light A1 and A2.

As illustrated in FIG. 4(b), when viewed from the direction d1, the phase of the excitation light L1 does not change in the SLM 14. From the above, sheet-like excitation light L1 is generated at a predetermined image formation position Y1. In this example, the sheet-like excitation light L1 is generated on the optical axis X such that a width direction thereof is the direction d2.

As described above, in the light-sheet microscope 1, the phase pattern P is calculated based on the basic phase pattern 31 having the first region 32 in which the phase value continuously increases in the direction D1 and the second region 33 in which the phase value continuously decreases in the direction D1. By modulating the excitation light with the SLM 14 in accordance with the phase pattern P, it is possible to irradiate the sample S with the sheet-like excitation light L1 from the first objective lens 16. Therefore, it is unnecessary to scan a light focus point of a Bessel beam in order to generate sheet-like excitation light L1 as in the conventional technology, and an optical element or the like for the scanning can be omitted. Consequently, according to the light-sheet microscope 1, it is possible to generate sheet-like excitation light L1 with a simple configuration. Furthermore, because it is unnecessary to scan the light focus point of the Bessel beam in order to generate the sheet-like excitation light L1 as in the conventional technology, it is possible to simplify control and shorten a time required for image acquisition.

In the light-sheet microscope 1, the phase value linearly increases in the direction D1 in the first region 32, and the phase value linearly decreases in the direction D1 in the second region 33. Thereby, because the basic phase pattern 31 is simplified, it is possible to generate sheet-like excitation light L1 with a simpler configuration without using complex optical elements or the like. That is, if the phase value does not linearly increase in the direction D1 in at least one of the first region 32 and the second region 33, a configuration of a first optical system 15 for generating the sheet-like excitation light L1 or an optical system such as the first objective lens 16 may be complicated. On the other hand, because the phase value increases linearly in the direction D1 in both the first region 32 and the second region 33 in the light-sheet microscope 1, it is possible to simplify the configuration of the optical system for generating the sheet-like excitation light L1.

In the light-sheet microscope 1, the basic phase pattern 31 is axisymmetric with respect to the straight line C. Thereby, it is possible to generate sheet-like excitation light L1 on the optical axis X of the first objective lens 16. Consequently, adjustment of optical axes of the first objective lens 16 and the second objective lens 17 is facilitated.

In the light-sheet microscope 1, the first region 32 and the second region 33 are adjacent to each other, and the phase value is continuous at the boundary. Thereby, because the basic phase pattern 31 is simplified, it is possible to generate sheet-like excitation light L1 with a simpler configuration without using complex optical elements or the like.

In the light-sheet microscope 1, because the optical scanning unit 13 for scanning the sample S with the excitation light L1 is provided, an irradiation position of the excitation light L1 radiated from the first objective lens 16 can be scanned with respect to the sample S.

In the light-sheet microscope 1, the photodetector 20 is a two-dimensional imaging element having a plurality of pixel columns R and in which rolling reading is possible. Thereby, S/N ratio can be improved as compared with a case in which a two-dimensional imaging element in which global reading is possible is used.

Figure 5:
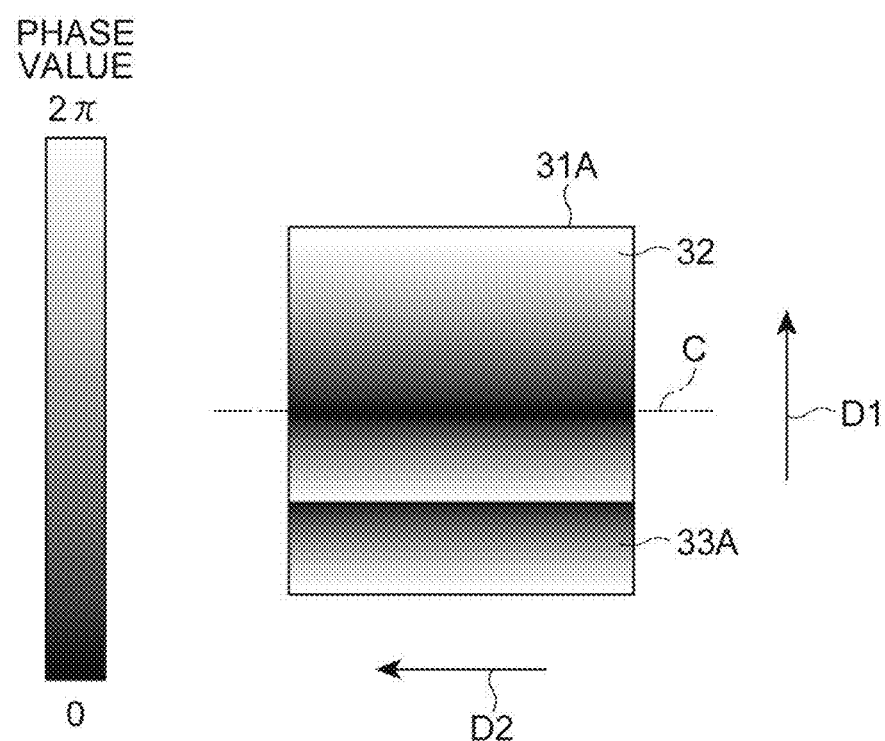
FIG. 5 is a diagram illustrating a first modified example of the basic phase pattern.

Although preferred embodiments of the present invention have been described above, the present invention is not limited to the above-described embodiments. For example, a basic phase pattern 31A of the first modification illustrated in FIG. 5 may be used. In a second region 33A of the basic phase pattern 31A, the phase value linearly decreases by $4\pi$ radians in the direction D1. That is, an absolute value of a gradient of a phase value in the first region 32 is different from an absolute value of a gradient in the second region 33A. The basic phase pattern 31A is non-axisymmetric with respect to the central line C. Also, in this example, the boundary between the first region 32 and the second region 33A is located on the central line C.

Figure 6:
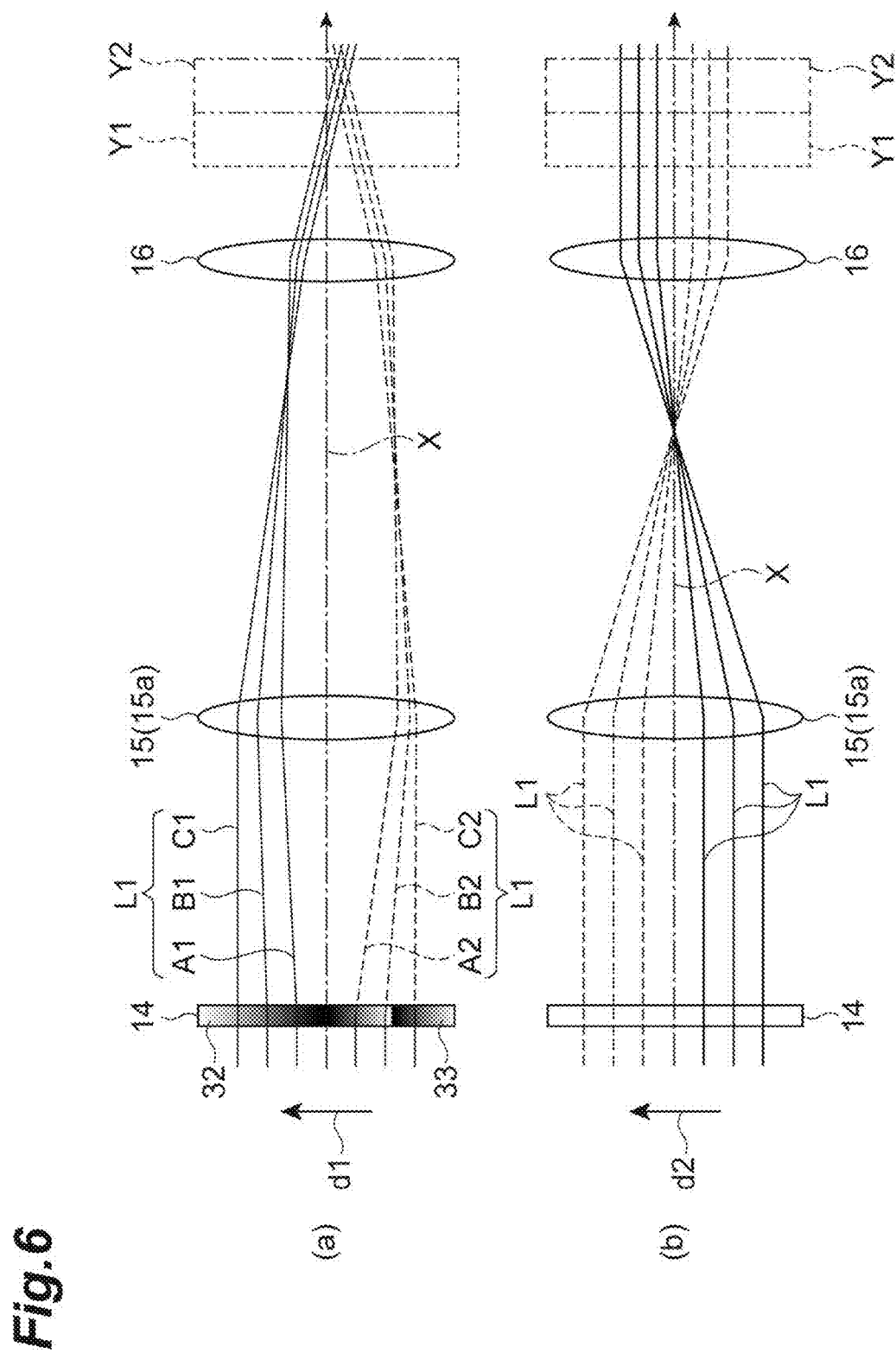
FIG. 6 is a conceptual diagram illustrating a state in which sheet-like excitation light is generated using the basic phase pattern of FIG. 5.

Even when such a basic phase pattern 31A is used, the excitation light L1 is modulated by the SLM 14 in accordance with the basic phase pattern 31A to generate sheet-like excitation light L1 as illustrated in FIG. 6. In this case, as illustrated in FIG. 6(a), an amount of phase delay in the excitation light A2 incident on the second region 33A in the SLM 14 is larger than that in the excitation light A1 incident on the first region 32. Likewise, an amount of phase delay in the excitation light B2 in the SLM 14 is larger than that in the excitation light B1 and an amount of phase delay in the excitation light C2 in the SLM 14 is larger than that in the excitation light C1. Thereby, sheet-like excitation light L1 is generated at an image formation position Y2 which is farther from the first objective lens 16 than an image formation position Y1 in the case of the above-described embodiment. This sheet-like excitation light L1 is generated at a position different from that on the optical axis X.

In this manner, in a first modified example, as in the case of the above-described embodiment, it is also possible to irradiate the sample S with sheet-like excitation light L1 from the first objective lens 16 and generate sheet-like excitation light L1 with a simple configuration. Also, because the basic phase pattern 31 is non-axisymmetric with respect to the straight line C in the first modified example, sheet-like excitation light L1 can be generated at a position different from that on the optical axis X of the first objective lens 16.

Figure 7:
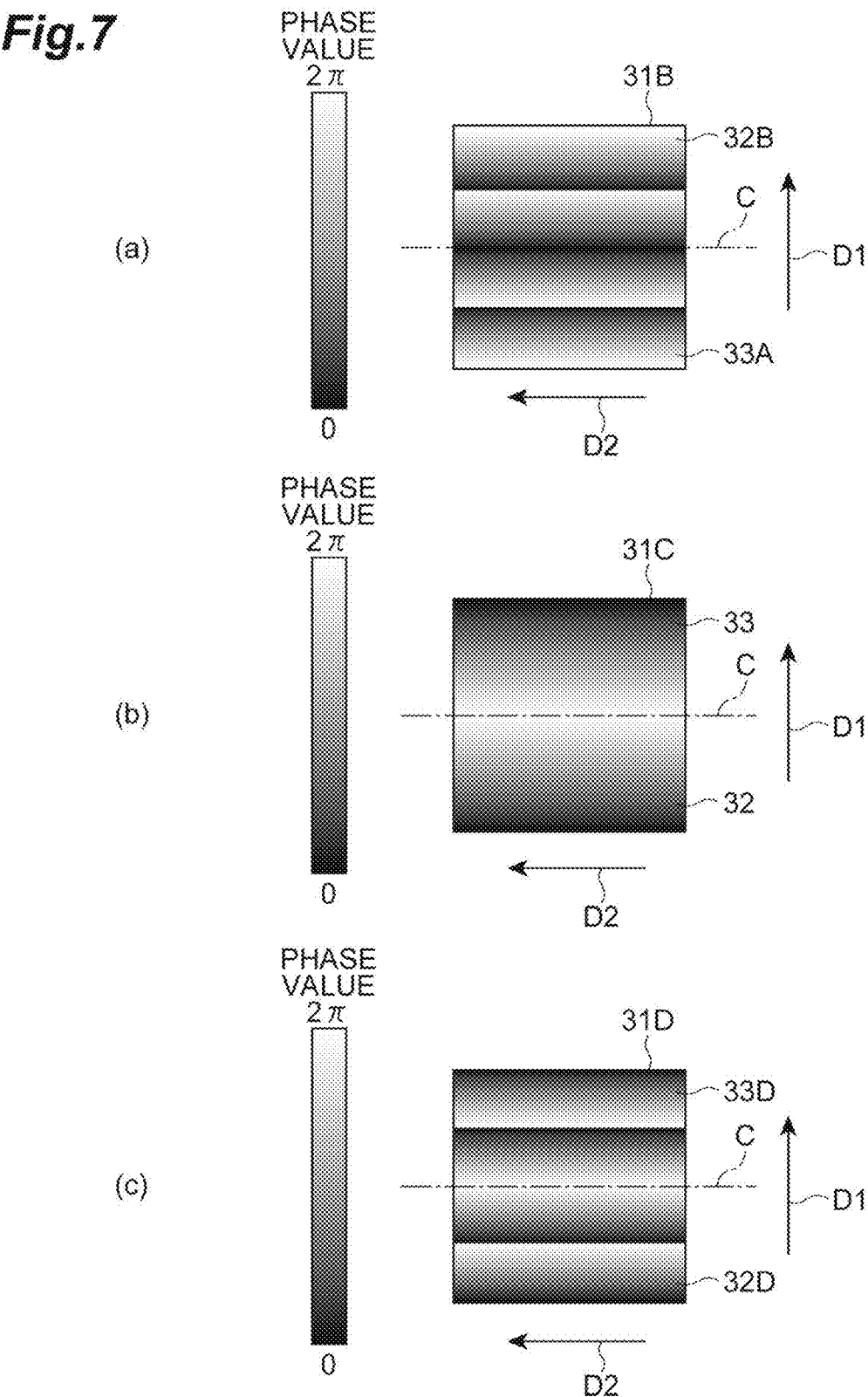
FIG. 7 is a diagram illustrating second to fourth modified examples of the basic phase pattern.

A basic phase pattern 31B of a second modified example, a basic phase pattern 31C of a third modified example, or a basic phase pattern 31D of a fourth modified example illustrated hi FIG. 7 may be used. In the first region 33B of the basic phase pattern 31B, the phase value linearly increases by $4\pi$ radians in the direction D1. That is, an absolute value of a gradient of the phase value in the first region 32B is equal to an absolute value of a gradient of the phase value in the second region 33A.

In the basic phase pattern 31C, a positional relationship between a first region 32 and a second region 33 in the direction D1 is opposite to that in the above-described embodiment. That is, in the above-described basic phase pattern 31, the phase value increases as the distance from the boundary (the central line C) increases in the first region 32 and the phase value decreases as the distance from the boundary decreases in the second region 33. On the other hand, in the above-described basic phase pattern 31C, the phase value increases as the distance from the boundary decreases in the first region 32 and the phase value decreases as the distance from the boundary increases in the second region 33.

In the basic phase pattern 31D, as in the above-described third modified example, a positional relationship between a first region 32D and a second region 33D in the direction D1 is opposite to that in the above-described embodiment. Further, in the basic phase pattern 31D, the phase value linearly increases by $4\pi$ radians in the direction D1 in the first region 32D and the phase value linearly decreases by $4\pi$ radians in the direction D1 in the second region 33D. The basic phase patterns 31B to 31D are axisymmetric with respect to the central line C. Also in the basic phase patterns 31B to 31D, the boundary between the first region 32 and the second region 33A is located on the central line C.

Even when these basic phase patterns 31B to 31D are used, it is possible to irradiate the sample S with the sheet-like excitation light L1 from the first objective lens 16 and it is possible to generate the sheet-like excitation light L1 with a simple configuration as in the case of the above-described embodiment.

Figure 8:
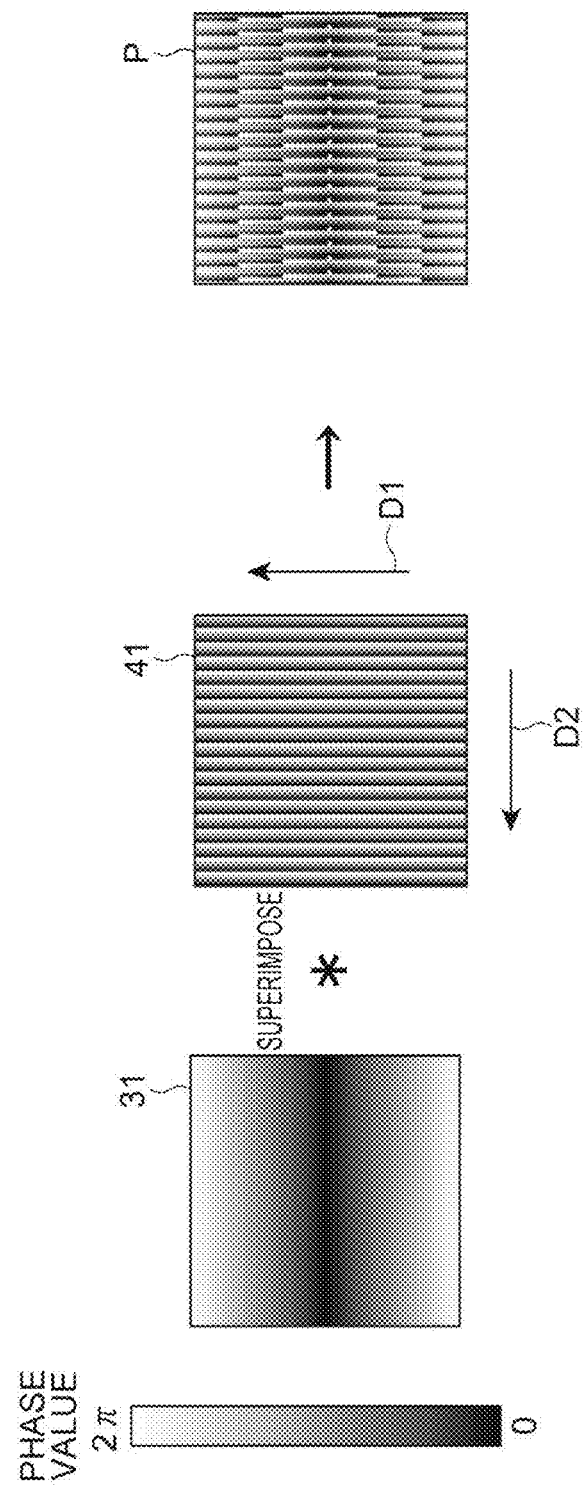
FIG. 8 is a diagram illustrating a state in which a diffraction grating pattern is superimposed on the basic phase pattern.
Figure 9:
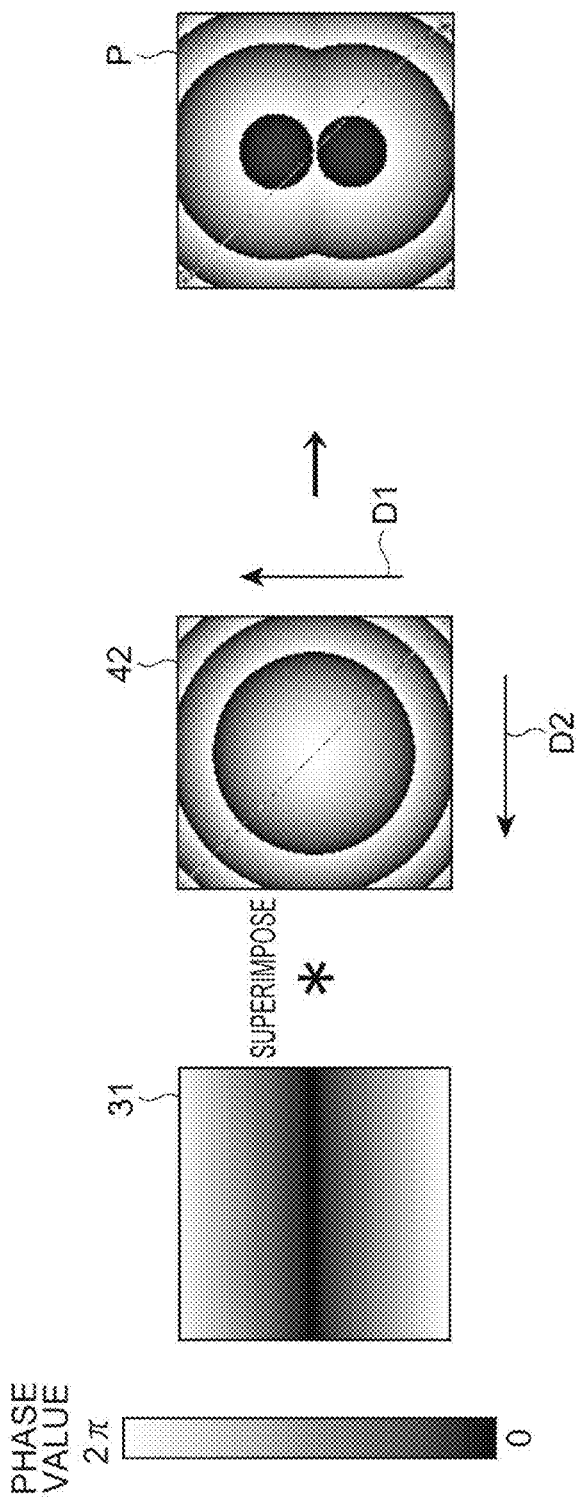
FIG. 9 is a diagram illustrating a state in which a lens pattern is superimposed on the basic phase pattern.

As illustrated in FIG. 8, the phase pattern P may be calculated by superimposing a diffraction grating pattern 41 of a diffraction grating shape on the basic phase pattern 31. The diffraction grating pattern 41 has the diffraction grating shape in the direction D2. Also, as illustrated in FIG. 9, for example, the phase pattern P may be calculated by superimposing a lens-like lens pattern 42 such as a Fresnel lens on the basic phase pattern 31. Also, the phase pattern P may be calculated by superimposing the diffraction grating pattern 41 or the lens pattern 42 on the basic phase patterns 31A to 31C.

In these cases, as in the case of the above-described embodiment, it is also possible to irradiate the sample S with sheet-like excitation light L1 from the first objective lens 16 and it is also possible to generate the sheet-like excitation light L1 with a simple configuration. Also, it is possible to form a phase of the excitation light in a diffraction grating shape or a lens shape without providing a diffraction grating or a lens element. Thus, it is possible to generate sheet-like excitation light L1 with a simpler configuration.

Figure 10:
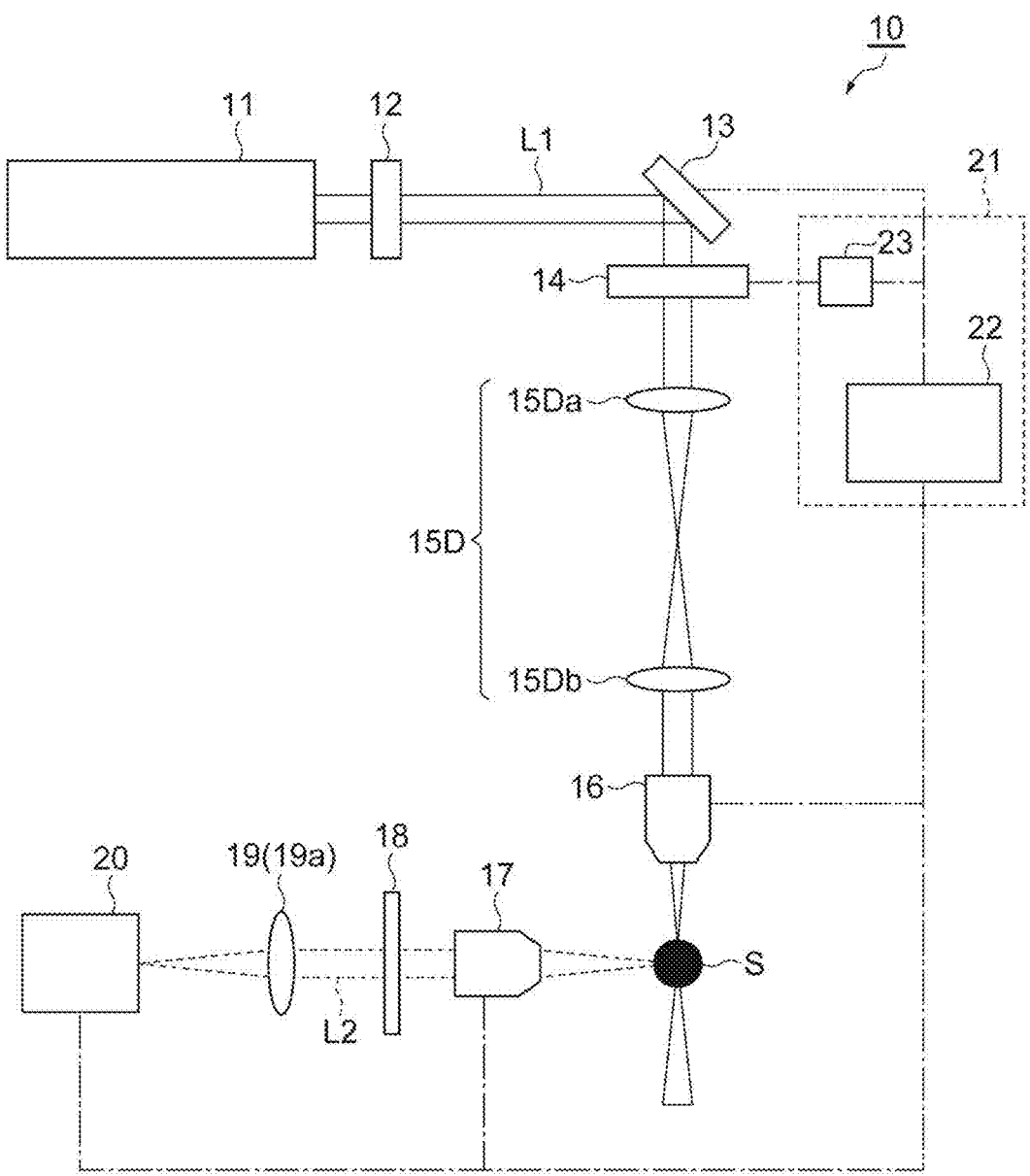
FIG. 10 is a block diagram illustrating a configuration of a light-sheet microscope according to a fifth modified example.

A configuration similar to that of a light-sheet microscope 1D of the fifth modified example illustrated in FIG. 10 may be adopted. The light-sheet microscope 1D is different from the light-sheet microscope 1 of the above-described embodiment in that a first optical system 15D constituting a telescope optical system is provided. The first optical system 15D includes two lenses 15Da and 15Db for causing excitation light L1 from the SLM 14 to be focused on the pupil of the first objective lens 16, and constitutes a telescope optical system. Examples of such a telescope optical system include a 4f optical system, a Keplerian type optical system, a Galilean type optical system, and the like. The first optical system 15D and the first objective lens 16 constitute an irradiation optical system.

Also with such a light-sheet microscope 1D, as illustrated in FIG. 11, excitation light L1 is modulated by the SLM 14 in accordance with the basic phase pattern 31 to generate sheet-like excitation light L1. In this manner, in the fifth modified example, as in the case of the above-described embodiment, it is possible to irradiate the sample S with the sheet-like excitation light L1 from the first objective lens 16 and generate the sheet-like excitation light L1 with a simple configuration.

In the basic phase pattern 31 of the above embodiment, a third region in which the phase value is constant in the direction D1 may be further provided. Such a third region may be provided, for example, between the first region 32 and the second region 33. In this case, the first region 32 and the second region 33 are not adjacent to each other.

In the above-described embodiment, the photodetector 20 may be a global readable area image sensor. The first optical system 15 may be omitted and the excitation light L1 output from the SLM 14 may be directly input to the first objective lens 16. The optical scanning unit 13 may be arranged to receive the excitation light L1 output from the SLM 14. The optical axis of the first objective lens 16 and the optical axis of the second objective lens 17 do not have to be orthogonal to each other and may not intersect each other.

The control unit 21 may control a wavelength, a sheet thickness, a light focus position, a shape, or the like of the sheet-like excitation light L1 to be generated by appropriately changing the phase pattern P. The control unit 21 may calculate the phase pattern P by superimposing a pattern for aberration correction on the basic phase pattern 31. This aberration correction pattern may be created based on image data output from the photodetector 20. Thereby, it is possible to perform feedback correction. For example, an optical element having a slit for cutting off zero-order light or higher-order light of the excitation light L1 may be provided between the lens 15a and the first objective lens 16. Thereby, unnecessary light (light serving as noise) can be shielded.

The control unit 21 may set the number of pixel columns N to be simultaneously exposed in the photodetector 20 in which rolling reading is possible in accordance with the phase pattern P. At this time, the control unit 21 sets a reading period T2 for rolling reading based on the set number of pixel columns N and an exposure period T1 of each pixel column. In this case, the exposure period T1 of each pixel column is set by the user or the like. The control unit 21 may set the exposure period T1 of each pixel column based on the set number of pixel columns N and the reading period T2 for rolling reading. In this case, the reading period T2 for rolling reading is set by the user or the like. In either case, the control unit 21 controls the optical scanning unit 13 or the photodetector 20 so that the scanning of the excitation light L1 by the optical scanning unit 13 and the signal reading of each pixel column R by the photodetector 20 in which rolling reading is possible are synchronized.

The irradiation optical system and the detection optical system may not include the objective lens. In this case, a condensing lens may be used instead of the first objective lens 16 or the second objective lens 17.

REFERENCE SIGNS LIST

1: Light-sheet microscope (image acquisition device), 11: Light source, 13: Optical scanning unit, 14: Spatial light modulator, 16: First objective lens, 17: Second objective lens, 20: Photodetector, 21: Control unit, 22: Computer, 23: Controller, 31: Basic phase pattern, 32: First region, 33: Second region, 41: Diffraction grating pattern, 42: Lens pattern, C: Straight line (central line), D1: Predetermined direction, L1: Excitation light, L2: Detection light, P: Phase pattern, R: Pixel column, S: Sample

The invention claimed is:

1. An image acquisition device comprising:
a light source configured to output excitation light including a wavelength for exciting a sample;
a spatial light modulator having a plurality of pixels two-dimensionally arranged and configured to modulate a phase of the excitation light for each of the plurality of pixels;
an irradiation optical system configured to radiate the modulated excitation light to the sample;
a detection optical system configured to form an image of detection light emitted from the sample in association with irradiation of the excitation light from the irradiation optical system;
a photodetector configured to capture the image of the detection light formed by the detection optical system; and
a controller configured to control an amount of phase modulation for each of the plurality of pixels in accordance with a phase pattern in which phase values corresponding to the plurality of pixels are two-dimensionally distributed, the phase pattern generated based on a predetermined basic phase pattern including a first region in which the phase value continuously increases in a predetermined direction and a second region in which the phase value continuously decreases in the predetermined direction and facing the first region in the predetermined direction,
wherein in both the first region and the second region, the phase value is constant in a direction orthogonal to the predetermined direction.

2. The image acquisition device according to claim 1, wherein the phase value linearly increases in the predetermined direction in the first region and the phase value linearly decreases in the predetermined direction in the second region.

3. The image acquisition device according to claim 1, wherein the basic phase pattern is axisymmetric with respect to a straight line passing through a center in the predetermined direction and orthogonal to the predetermined direction.

4. The image acquisition device according to claim 1, wherein the basic phase pattern is non-axisymmetric with respect to a straight line passing through a center in the predetermined direction and orthogonal to the predetermined direction.

5. The image acquisition device according to claim 1, wherein the first region and the second region are adjacent to each other and the phase values are continuous at a boundary therebetween.

6. The image acquisition device according to claim 1, wherein the phase pattern is a phase pattern in which a diffraction grating pattern of a diffraction grating shape and the basic phase pattern are superimposed on each other.

7. The image acquisition device according to claim 1, wherein the phase pattern is a phase pattern in which a lens pattern of a lens shape and the basic phase pattern are superimposed on each other.

8. The image acquisition device according to claim 1, further comprising:
a light scanner configured to scan the sample with the excitation light.

9. The image acquisition device according to claim 1, wherein the photodetector is an area image sensor having a plurality of pixel columns and in which rolling reading is enabled.

10. The image acquisition device according to claim 1, wherein the image acquisition device is a light-sheet microscope.

11. An image acquisition method comprising:
modulating, by a spatial light modulator having a plurality of pixels two-dimensionally arranged, a phase of excitation light including a wavelength for exciting a sample for each of the plurality of pixels, the modulating including controlling an amount of phase modulation for each of the plurality of pixels in accordance with a phase pattern generated based on a predetermined basic phase pattern and in which phase values corresponding to the plurality of pixels are two-dimensionally distributed, the basic phase pattern including a first region in which the phase value continuously increases in a predetermined direction and a second region in which the phase value continuously decreases in the predetermined direction and facing the first region in the predetermined direction, wherein in both the first region and the second region, the phase value is constant in a direction orthogonal to the predetermined direction;
radiating the modulated excitation light to the sample; and
forming an image of detection light emitted from the sample in association with irradiation of the excitation light and capturing the formed image of the detection light.

12. A spatial light modulation unit for use in a light-sheet microscope, the spatial light modulation unit comprising:
a spatial light modulator having a plurality of pixels two-dimensionally arranged and configured to modulate a phase of input light for each of the plurality of pixels and to output modulated light; and
a controller configured to control an amount of phase modulation for each of the plurality of pixels in accordance with a phase pattern in which phase values corresponding to the plurality of pixels are two-dimensionally distributed, the phase pattern generated based on a predetermined basic phase pattern including a first region in which the phase value continuously increases in a predetermined direction and a second region in which the phase value continuously decreases in the predetermined direction and facing the first region in the predetermined direction, wherein in both the first region and the second region, the phase value is constant in a direction orthogonal to the predetermined direction.

* * * * *